US00PP29826P2

(12) United States Plant Patent
Burton

(10) Patent No.: US PP29,826 P2
(45) Date of Patent: Nov. 13, 2018

(54) ***COPROSMA* PLANT NAMED 'NGCOP6'**

(50) Latin Name: *Coprosma repens*
Varietal Denomination: NGCOP6

(71) Applicant: Stephen Burton, Cambridge (NZ)

(72) Inventor: Stephen Burton, Cambridge (NZ)

( * ) Notice: Subject to any disclaimer, the term of this patent is extended or adjusted under 35 U.S.C. 154(b) by 0 days.

(21) Appl. No.: 15/732,623

(22) Filed: Dec. 5, 2017

(51) Int. Cl.
*A01H 5/00* (2018.01)

(52) U.S. Cl.
USPC ..... Plt./226
CPC ..... *A01H 5/00* (2013.01)

(58) Field of Classification Search
USPC ..... Plt./226
CPC ..... A01H 5/00
See application file for complete search history.

*Primary Examiner* — Kent L Bell

(57) ABSTRACT

A new cultivar of *Coprosma* plant named 'NGCOP6' that is characterized by a compact habit, glossy leaves, young upper side leaves that are yellow-green in color with lighter yellow-green centers and red-orange margins and mature upper side leaves that are grey-purple in color with blotches of green.

1 Drawing Sheet

Botanical classification: *Coprosma repens.*
Variety denomination: 'NGCOP6'.

BACKGROUND OF THE INVENTION

The present invention relates to a new and distinct cultivar of *Coprosma* plant botanically known as *Coprosma repens* and hereinafter referred to by the cultivar name 'NGCOP6'.

The new cultivar was discovered by the inventor in a cultivated area of Cambridge, New Zealand in 2010. 'NGCOP6' was discovered as a naturally occurring branch mutation of *Coprosma* 'Tequila Sunrise' (U.S. Plant Pat. No. 18,392).

Asexual reproduction by tip cuttings of the new cultivar 'NGCOP6' was first performed in 2011 in Cambridge, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Coprosma* cultivar 'NGCOP6'.

1. *Coprosma* 'NGCOP6' exhibits a compact habit.
2. *Coprosma* 'NGCOP6' exhibits glossy leaves.
3. *Coprosma* 'NGCOP6' exhibits young upper side leaves that are yellow-green in color with lighter yellow-green centers and red-orange margins.
4. *Coprosma* 'NGCOP6' exhibits mature upper side leaves that are grey-purple in color with blotches of green.

The closest comparison cultivars are *Coprosma* 'Scarlett O'Hara' (not patented) and the parent plant *Coprosma* 'Tequila Sunrise'. The new cultivar 'NGCOP6' is distinguishable from 'Scarlett O'Hara' by the following characteristics:

1. 'NGCOP6' has young upper side leaves that are yellow-green in color with lighter yellow-green centers and red-orange margins. In comparison, the young upper side leaves of 'Scarlett O'Hara' are red.

2. 'NGCOP6' has mature upper side leaves that are grey-purple in color with blotches of green. In comparison, the mature upper side leaves of 'Scarlett O'Hara' are red-orange with red margins.

The new cultivar 'NGCOP6' is distinguishable from the parent plant 'Tequila Sunrise' by the following characteristics:

1. 'NGCOP6' has young upper side leaves that are yellow-green in color with lighter yellow-green centers and red-orange margins. In comparison, the young upper side leaves of 'Tequila Sunrise' have green centers surrounded by yellow areas with orange margins.
2. 'NGCOP6' has mature upper side leaves that are grey-purple in color with blotches of green. In comparison, the mature upper side leaves of 'Tequila Sunrise' have green centers surrounded by red areas with red margins.

BRIEF DESCRIPTION OF THE DRAWING

The accompanying photograph illustrates the distinguishing traits of *Coprosma* 'NGCOP6'. The plant in the photograph shows an overall view of a 12 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Coprosma* cultivar named 'NGCOP6'. Data was collected in Grand Haven, Mich. from 12 month old greenhouse grown plants in one gallon containers. The plants were grown under natural light. The time of year was Summer and the average temperature range was 18 to 27 degrees Centigrade during the day and 5 to 10 degrees Centigrade at night. No photoperiodic treatments or growth retardants were used. Color determinations are in accordance with The Royal Horticultural Society Colour Chart 2015 edition, except where general color terms of ordinary dictionary significance are used. The growing requirements are similar to the species. 'NGCOP6' has not been tested under all possible conditions and phenotypic differences may be observed with variations in environmental, climatic, and cultural conditions, however, without any variance in genotype.

Botanical classification: *Coprosma repens* 'NGCOP6'.

Use: Ornamental perennial.

Parentage: 'NGCOP6' is a naturally occurring branch mutation of *Coprosma* 'Tequila Sunrise'.

Vigor: Moderate.

Growth rate: Moderate.

Growth habit: Freely branching, dense, bushy habit.

Plant shape: Rounded, mounding.

Suitable container size: One gallon container.

Height: Average 18 cm. in height.

Width: Average 21 cm. in width.

Low temperature tolerance: −1 degrees Centigrade.

High temperature tolerance: 39 degrees Centigrade.

Propagation: Tip cuttings.

Time to initiate roots: Approximately 30 days in the Summer at 22 degrees Centigrade and 35 days in the Winter at 22 degrees Centigrade.

Time to produce a rooted cutting: Approximately 112 days in the Summer at 25 degrees Centigrade and 140 days in the Winter at 25 degrees Centigrade.

Crop time: Approximately 12 months.

Root system: Fibrous, densely matted.

Root color: 165D.

Lateral branches:

*Branching habit*.—Freely branching.

*Basal branching*.—Yes.

*Quantity*.—Approximately 8.

*Dimensions*.—15.0 cm. in length and 4.0 mm. in diameter.

*Internode length*.—12.5 mm.

*Stem color*.—195A.

*Stem shape*.—Round in cross-section.

*Stem pubescence*.—Sparsely covered with short hairs.

*Stem aspect*.—0 to 35 degrees from vertical.

*Stem strength*.—Strong.

*Pinching*.—Yes.

Foliage:

*Leaf arrangement*.—Opposite.

*Compound or single*.—Single.

*Leaf shape*.—Ovate.

*Leaf apex*.—Acute.

*Leaf base*.—Cuneate.

*Leaf length*.—Average 3.5 cm. in length.

*Leaf width*.—Average 1.75 cm. in width.

*Leaf texture*.—Smooth, waxy both surfaces.

*Leaf luster*.—Glossy both surfaces.

*Leaf pubescence*.—Absent.

*Leaf margin*.—Entire, unevenly recurved, slightly wavy.

*Vein pattern*.—Pinnate.

*Young leaf color* (*upper surface*).—144A, center 154B, margins N34A.

*Young leaf color* (*lower surface*).—N144C.

*Mature leaf color* (*upper surface*).—187A with blotches of 143B.

*Mature leaf color* (*lower surface*).—A mixture of 145C and 46C.

*Vein color* (*upper surface*).—Same as leaf color.

*Vein color* (*lower surface*).—46D.

*Durability of foliage to stress*.—Moderate to high.

*Leaf attachment*.—Petiolate.

Petiole:

*Petiole dimensions*.—1.0 cm. in length and 2.0 mm. in diameter.

*Petiole texture*.—Smooth.

*Petiole pubescence*.—Absent.

*Petiole color*.—174B.

Flowers: *Coprosma* 'NGCOP6' has not produced flowers to date.

Disease and insect resistance: Plants of the new *Coprosma* have not been observed for disease or insect resistance.

The invention claimed is:

1. A new and distinct variety of *Coprosma* plant named 'NGCOP6' as described and illustrated.

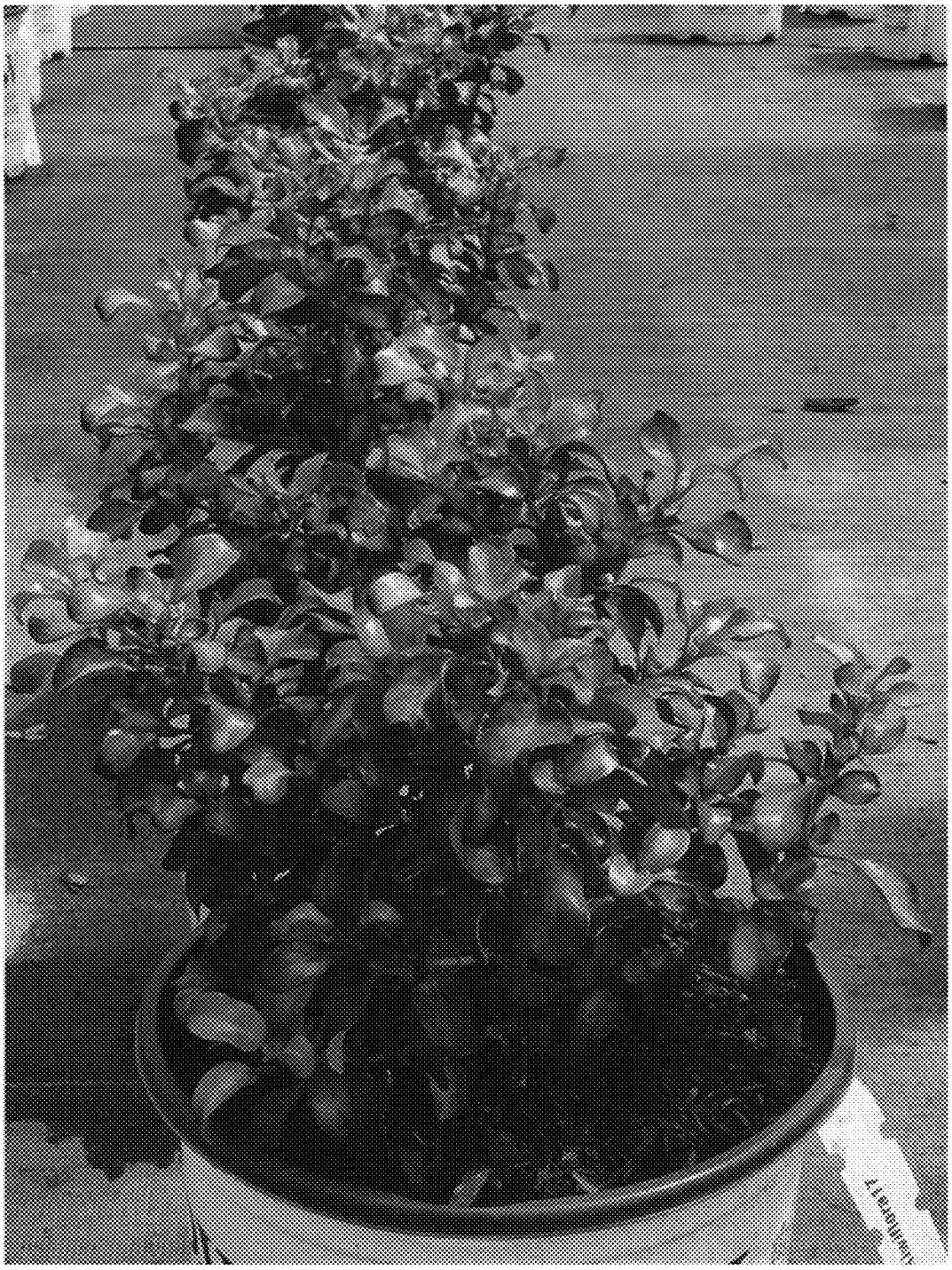

* * * * *